US009637561B2

United States Patent
Gatenholm

(10) Patent No.: US 9,637,561 B2
(45) Date of Patent: May 2, 2017

(54) PLASTICIZER-FREE FLEXIBLE OXYGEN BARRIER FILMS AND LAMINATES BASED ON NEGATIVELY CHARGED AND ACETYLATED NON-CELLULOSIC POLYSACCHARIDES ISOLATED FROM BIOMASS

(75) Inventor: Paul Gatenholm, Riner, VA (US)

(73) Assignee: Advanced Polymer Technology AB, Kullavik (SE)

( * ) Notice: Subject to any disclaimer, the term of this patent is extended or adjusted under 35 U.S.C. 154(b) by 804 days.

(21) Appl. No.: 13/984,209

(22) PCT Filed: Feb. 8, 2012

(86) PCT No.: PCT/US2012/024331
§ 371 (c)(1),
(2), (4) Date: Oct. 28, 2013

(87) PCT Pub. No.: WO2012/109357
PCT Pub. Date: Aug. 16, 2012

(65) Prior Publication Data
US 2014/0044981 A1    Feb. 13, 2014

Related U.S. Application Data

(60) Provisional application No. 61/440,850, filed on Feb. 8, 2011.

(51) Int. Cl.
*C08B 37/00*   (2006.01)
*C08B 37/14*   (2006.01)
(Continued)

(52) U.S. Cl.
CPC ............ *C08B 37/006* (2013.01); *B65D 81/18* (2013.01); *C08B 37/0003* (2013.01);
(Continued)

(58) Field of Classification Search
CPC ... C08B 37/0003; C08B 37/0057; C08L 5/14; C08H 8/00; Y10T 428/31986; C12P 2201/00; D21H 21/16
See application file for complete search history.

(56) References Cited

U.S. PATENT DOCUMENTS

| 7,427,643 B2 | 9/2008 | Gatenholm et al. |
| 2001/0020091 A1* | 9/2001 | Buchanan et al. ..... A23D 9/007 536/123 |

FOREIGN PATENT DOCUMENTS

| WO | 2004083286 A | 9/2004 |
| WO | 2012109357 A | 8/2012 |

OTHER PUBLICATIONS

Hollmann et al., "Pilot-scale isolation of glucuronoarabinoxylans from wheat bran," Carbohydrate Polymers, vol. 59, pp. 225-230 (2005).*

(Continued)

*Primary Examiner* — Randy Gulakowski
*Assistant Examiner* — Ha S Nguyen
(74) *Attorney, Agent, or Firm* — New River Valley IP Law, PC; Michele L. Mayberry

(57) ABSTRACT

Food, consumer, and industrial product packaging materials are provided by embodiments of the present invention. Films and laminates based on a combination of negatively charged polysaccharides are provided as such packaging materials. The films can be prepared by mildly treating soft wood with steam followed by alkali extraction and enzymatic treatment. Negatively charged non-cellulosic polysaccharides are isolated with weight average molecular weight Mw higher than 10,000 g/mol and molecular structure comprising a xylan main chain substituted with more than 15 molar % of glucuronic acid and more than 5 molar % arabinose. The negatively charged non-cellulosic polysaccharides can be casted from water solution on a suitable (Continued)

carrier and surface acetylated or coated with acetylated polysaccharide to obtain oxygen and water barrier packaging laminate. Inventive packaging materials can have strength at break above 55 MPa, elongation to break above 2.5%, cohesive and adhesive properties and good oxygen and moisture barrier properties.

18 Claims, 3 Drawing Sheets

(51) Int. Cl.
<table>
<tr><td>C08L 5/14</td><td>(2006.01)</td></tr>
<tr><td>C08H 8/00</td><td>(2010.01)</td></tr>
<tr><td>C12P 19/04</td><td>(2006.01)</td></tr>
<tr><td>D21C 5/00</td><td>(2006.01)</td></tr>
<tr><td>B65D 81/18</td><td>(2006.01)</td></tr>
<tr><td>D21H 27/10</td><td>(2006.01)</td></tr>
<tr><td>D21H 21/16</td><td>(2006.01)</td></tr>
</table>

(52) U.S. Cl.
CPC ........... *C08B 37/0057* (2013.01); *C08H 8/00* (2013.01); *C08L 5/14* (2013.01); *C12P 19/04* (2013.01); *D21C 5/005* (2013.01); *D21H 27/10* (2013.01); *C12P 2201/00* (2013.01); *D21H 21/16* (2013.01); *Y10T 428/31986* (2015.04)

(56) References Cited

OTHER PUBLICATIONS

Ebringerova et al., "Xylan and xylan derivatives—biopolymers with valuable properties, 1 Naturally occurring xylan structures, isolation procedures and properties," Macromolecular Rapid Communications, vol. 21, pp. 542-556 (2000).*
Ceusters, J. et al. "Glucuronoarabinoxylan Structure in the Walls of Aechmea . . . ", Phytochemistry (2008) vol. 69, pp. 2307-2311.
Claus J. Weber, "Biobased Packaging Materials for the Food Industry Status and Perspectives", a European Concerted Action, Nov. 2000.
Jacobs et al., "Characterization of Water-Soluble Hemicelluloses . . . ", Carbohydrate Research (2002) vol. 337, pp. 711-717.
Kay Cooksey, "Important Factors for Selecting Food Packaging Materials Based on Permeability", Flexible Packaging Conference, 2004.
Lindblad et al., Modified Galactoglucomannans from Forestry Waste-Water . . . , ACS Symposium Series (2009) vol. 1017, pp. 185-198.
PCT International Preliminary Report on Patentability for Co-Pending International Application No. PCT/US2012/024331 dated Aug. 22, 2013.
PCT International Search Report and Written Opinion for Co-Pending Application No. PCT/US2012/024331 dated Aug. 24, 2012.
Shulami et al., "The Glucuronic Acid Utilization Gene Cluster . . . ", J. Bacteriol (1999) vol. 181, pp. 3695-3704.
Viikari et al., "Enzymatic Accessibility of Xylans . . . ", Appl. Microbiol. Biotechnol. (1994) vol. 41, pp. 124-129.

* cited by examiner

PLASTICIZER-FREE FLEXIBLE OXYGEN BARRIER FILMS AND LAMINATES BASED ON NEGATIVELY CHARGED AND ACETYLATED NON-CELLULOSIC POLYSACCHARIDES ISOLATED FROM BIOMASS

CROSS-REFERENCE TO RELATED APPLICATIONS

The present application is a National Stage application under 35 USC §371 of Application No. PCT/US12/24331, filed Feb. 8, 2012, which application claims priority to and the benefit of the filing date of U.S. Provisional Patent Application No. 61/440,850, filed Feb. 8, 2011, the disclosures of which are hereby incorporated by reference herein in their entireties.

BACKGROUND OF THE INVENTION

Field of the Invention

The present invention relates to food packaging materials, industrial product packaging materials and packaging for consumer products. More particularly, embodiments of the present invention relate to films and laminates based on a combination of negatively charged polysaccharides, such as glucuronoarabinoxylans and acetylated polysaccharides, such as acetylated arabinoxylans and processes for the isolation of these polysaccharides from biomass and particularly soft wood.

Packaging materials have shifted from metal to glass and recently to plastic based on fossil resources. The use of packaging materials particularly for food and industrial products is expected to increase dramatically in the nearest future. The access to renewable raw materials is crucial for sustainable development. Biomass based biopolymers have great potential to be used as packaging materials. The lack of effective isolation processes and lack of understanding of structure-property relationship has delayed extensive use of the biomass based biopolymers as packaging materials. Among biomass based biopolymers only cellulose fibers are used as board or paper in packaging. The advantage of renewability and potential composting is lost when cellulose based board is laminated with aluminum and fossil fuel based plastics.

Non-cellulosic polysaccharides such as glucuronoarabinoxylans are biosynthesized in most plants and, together with cellulose fibers and lignin, they are the most important plant biopolymers. Wood and annual plants can be considered as complex composite materials where cellulose microfibrils constitute the load-carrying framework, and lignin is the matrix substance. The non-cellulosic polysaccharides are associated both with the cellulose microfibrils and the lignin matrix. Non-cellulosic polysaccharides have been shown to play an important role as regulators of cellulose aggregation, resulting in formation of secondary and tertiary structures of the cell wall. Non-cellulosic polysaccharides have not yet been utilized industrially as raw material for packaging. The major reason for this is the fact that the current isolation processes which are designed for isolation of cellulosic component contribute to severe degradation of non-cellulosic polysaccharides with loss of inherent material properties.

The use of polysaccharides as films to protect food from oxygen has been described in International Patent Application Publication No. WO 2004/083286. The polysaccharides described in International Patent Application Publication No. WO 2004/083286 are hemicelluloses and the use is as films. The polymers described in International Patent Application Publication No. WO 2004/083286 do not form films without plasticizers. They are also water sensitive. All references described in this specification are incorporated by reference herein in their entireties.

What is needed, however, is a flexible yet strong food packaging material with superior oxygen and/or moisture barrier characteristics in a bio-based packaging material.

SUMMARY OF THE INVENTION

The present invention describes isolation and use of negatively charged non-cellulosic polysaccharides particularly glucuronoarabinoxylans from biomass, preferable softwood and their use as oxygen barrier in laminates. The upper part of the laminates is acetylated which provides a good moisture barrier. Glucuronoarabinoxylans, particularly ones isolated from soft wood are capable of providing excellent flexibility to laminates and good oxygen barrier properties without addition of plasticizer.

We have developed an isolation process in which biomass, preferably soft wood is mildly treated with steam followed by alkali extraction and enzymatic treatment. In this process negatively charged non-cellulosic polysaccharides can be isolated with weight average molecular weight $M_w$ higher than 10,000 g/mol and molecular structure which consists of xylan main chain substituted with more than 15 molar % of 4-O-methyl-glucuronic acid and more than 5 molar % arabinose. Such negatively charged non-cellulosic polysaccharides are casted from water solution on suitable carrier which can be cellulose based board or polymeric film. They form flexible films without addition of external plasticizer and exhibit excellent oxygen barrier properties ($O_2$ permeability equal or less than 0.12 cm$^3$ μm m$^{-2}$ d$^{-1}$ kPa$^{-1}$).) Such films can be surface acetylated or coated with acetylated polysaccharide to obtain oxygen and water barrier packaging laminate.

The most desirable properties of packaging materials are good mechanical properties including strength at break above 55 MPa, flexibility which is provided by elongation to break higher than 2.5%, cohesive and adhesive properties and good oxygen and moisture barrier properties. The process of isolation of polysaccharides from biomass is preferably designed to preserve molecular structure which provides desired material properties and molecular weight. The present invention describes isolation, modification and preparation of films and laminates for packaging based on negatively charged non-cellulosic polysaccharides from biomass.

Biobased Packaging Materials for the Food Industry, Status and Perspectives, a European Concerted Action, Ed. Claus J. Weber, November 2000, ISBN 87-9050407-0, which is hereby incorporated by reference herein in its entirety, provides details of common desirable characteristics of various types of food packaging materials. Any one or more, and in any combination, of the features described in this cited reference can be incorporated into the products provided by the present invention.

Specifically provided by the invention is a process for obtaining non-cellulosic polysaccharides from biomass comprising: refining a biomass by grinding or ball milling; performing mild steaming and alkali extraction of the biomass; treating the extract by enzymatic treatment; and isolating negatively charged non-cellulosic polysaccharides with weight average molecular weight Mw higher than 10,000 g/mol and molecular structure comprising a xylan main chain substituted with more than 15 molar % of 4-O-methyl-glucuronic acid and more than 5 molar % arabinose.

Also included is a process for isolating glucuronoarabinoxylan from biomass comprising: obtaining a biomass; optionally mechanically processing the biomass; steam treating the biomass at a temperature and under conditions and for a time sufficient to facilitate extraction of non-cellulosic polysaccharides; optionally filtering and washing the steam treated biomass with ethanol; performing an alkaline ethanol extraction by: (i) preparing a mixture by mixing the steam treated biomass with about 70% ethanol in a liquid:solid ratio ranging from about 20:1 to 1:1 and adding alkali to a final concentration of about 1-5% by weight of the mixture; (ii) optionally heating the mixture at a temperature and under conditions and for a time sufficient to extract non-cellulosic polysaccharides; (iii) optionally treating the mixture with about 5% by weight alkali at a temperature and under conditions and for a time sufficient to extract non-cellulosic polysaccharides; (iv) obtaining a filtrate comprising the non-cellulosic polysaccharides and treating the filtrate with one or more enzymes of a type and amount sufficient to cleave lignin polysaccharide bonds to obtain glucuronoarabinoxylan; and preparing a precipitate of the glucuronoarabinoxylan by ethanol addition, drying the precipitate, and obtaining glucuronoarabinoxylan having at least 10% molar concentration of arabinose, at least 15% molar concentration of 4-O-methyl glucuronic acid, and a weight average molecular weight of at least 10,000 g/mol.

Soft wood can be used as the biomass in any process according to the invention.

In embodiments, the biomass can be steam treated using water at about 95 degrees C. for about 6 hours. Optionally, in extracting the polymer, the step of heating the mixture comprises heating at about 70 degree C. for about 3 hours. Optionally, the mixture can be treated with about 5% by weight alkali extract comprising treating at room temperature for about 10 hours. Even further, such processes can comprise treating the filtrate with one or more enzymes comprises treating with esterases.

A laminate comprising a substrate coated with negatively charged non-cellulosic polysaccharide prepared by any method described in this specification, and exhibiting oxygen barrier properties sufficient for packaging food or oxygen-sensitive materials is also encompassed by the invention.

Such laminates can be coated with acetylated arabinoxylan, or layered with a laminate coated in this manner.

Embodiments further provide a laminate comprising a substrate coated with negatively charged non-cellulosic polysaccharide prepared by the methods described above and/or in the examples of this specification and further surface acetylated. Such laminates and films can alternatively or in addition be layered with other laminates and films that are surface acetylated to provide a film with one surface having certain characteristics and a second opposing surface with different characteristics.

Food packaging materials comprising at least one laminate produced by the methods described in this specification, or at least one laminate described in this specification are also included as embodiments of the invention.

Also included are industrial product packaging materials comprising at least one laminate produced by any method described herein, or at least one laminate described herein.

Preferred are bio-based packaging materials, such as glucuronoarabinoxylan comprising materials having strength at break above 55 MPa, elongation to break above 2.5%, cohesive and adhesive properties and good oxygen and moisture barrier properties.

Such packaging materials preferably have one or more of the following characteristics: strength at break in the range of about 20 MPa to 100 MPa, such as from 25-80 MPa, or from about 30-75 MPa, or from about 35-70 MPa, or from about 40-65 MPa, or from about 45-60 MPa, or from about 50-62 MPa; elongation to break in the range of about 1-10%, such as from about 2-8%, or from about 3-9%, or from about 4-7%, or from about 5-6%; and/or comprises cohesive properties; and/or comprises adhesive properties; and/or comprises a partial or total barrier to oxygen; and/or comprises a partial or total barrier to moisture.

BRIEF DESCRIPTION OF THE DRAWINGS

The accompanying drawings illustrate certain aspects of some of the embodiments of the present invention, and should not be used to limit or define the invention. Together with the written description the drawings serve to explain certain principles of the invention.

DETAILED DESCRIPTION OF VARIOUS EMBODIMENTS OF THE INVENTION

Figure 1:
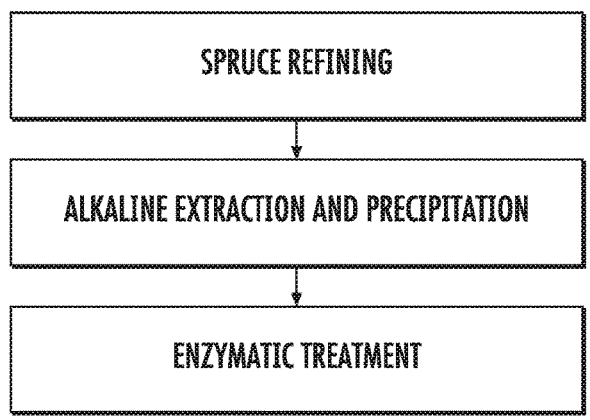
FIG. 1 is a schematic diagram illustrating an exemplary layout of an isolation process according to embodiments of the invention in which negatively charged non-cellulosic polysaccharides are isolated from biomass in a series of operation steps, which can include one or more or all of the following: refining, steaming, alkali extraction, and enzymatic treatment.
Figure 2:
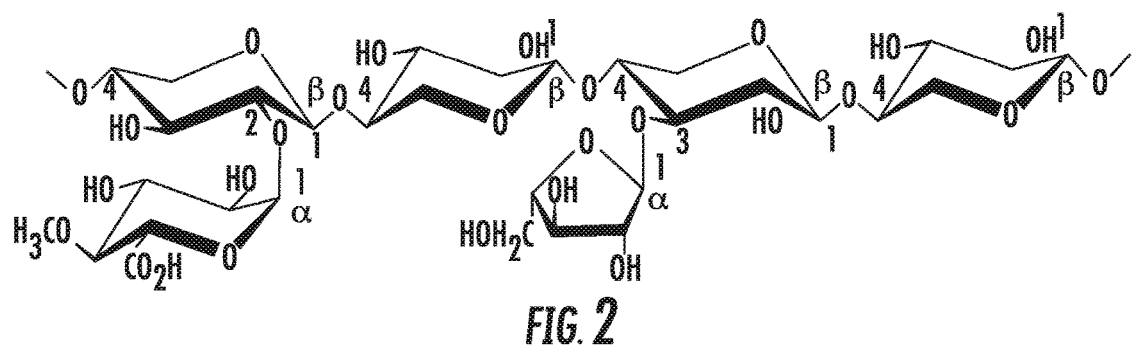
FIG. 2 is a schematic diagram showing the chemical structure of negatively charged non-cellulosic polysaccharides isolated from spruce in which the main chain consists of xylan and the xylan is substituted with 4-O-methyl glucuronic acid and arabinose.
Figure 3:
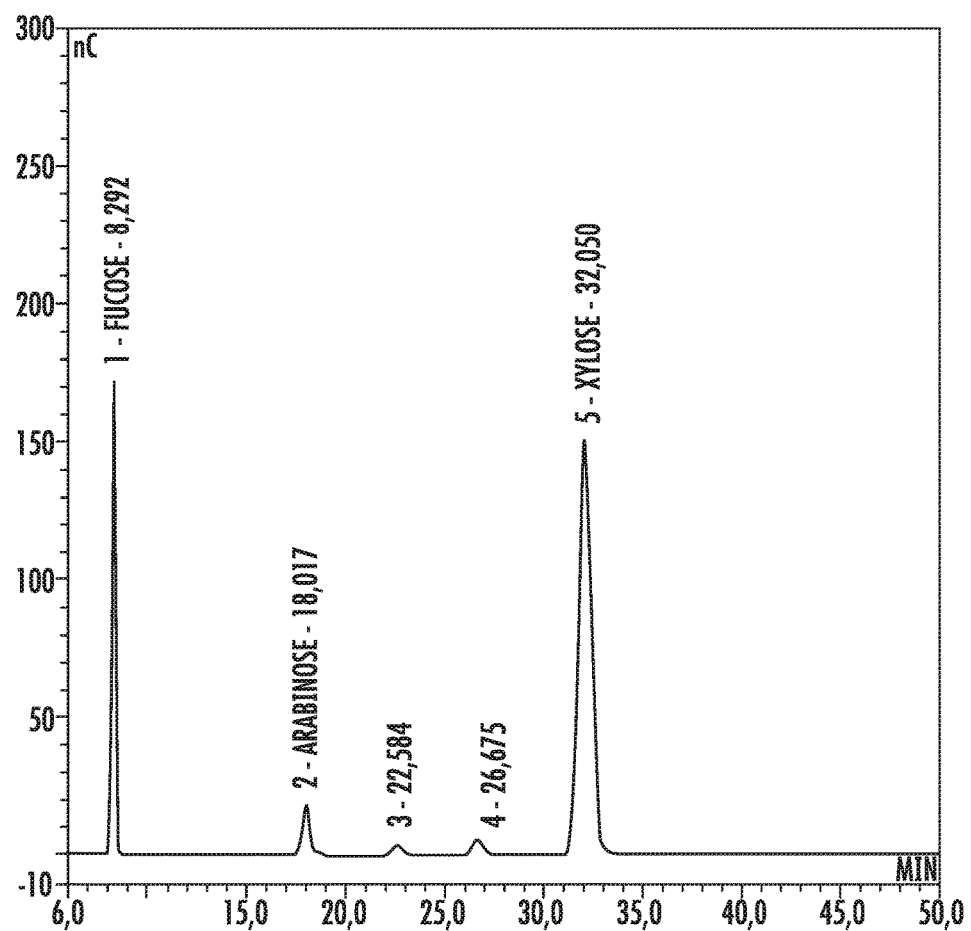
FIG. 3 is a chromatograph obtained by Dionex, which indicates xylan is substituted by 10% of arabinose.
Figure 4:
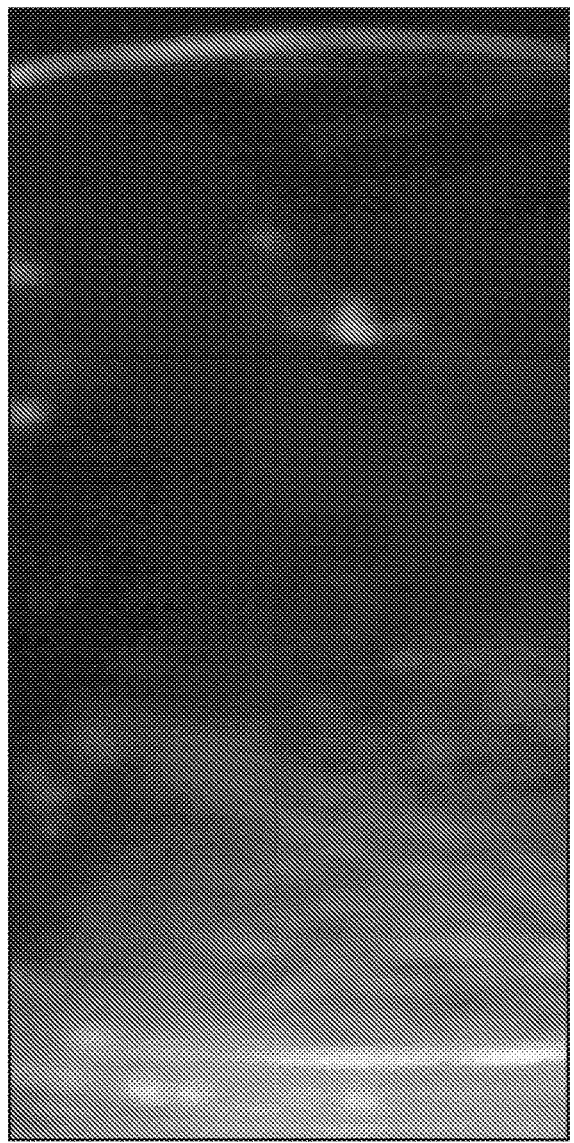
FIG. 4 is a photograph showing an embodiment of a flexible film prepared by casting 5% by weight water solution of glucuronoarabinoxylan.

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

EXAMPLES

Example 1

Isolation of Glucuronoararabinoxylans from Spruce

Norwegian spruce was refined using mechanically rotating disks. Refining of the biomass is optional. After refining, the wood meal was steamed with water at about 95 degrees C. for about 6 hours. The amount of time and temperature used can be varied. For example, the biomass can be steam treated at 80 degrees C. to 200 degrees C., such as from about 85 degrees C. to 150 degrees C., or from about 90 degrees C. to about 120 degrees C., or from about 100 degrees C. to about 110 degrees C. Likewise, steam treatment can be performed for any desired amount of time sufficient to partially decompose the material, such as from about 1 hour to 2 days. Indeed, the biomass can be exposed to steam treatment in the range of 2 hours to 1 day, such as from about 3 hours to 18 hours, or from about 4 hours to about 15 hours, or from about 5 hours to about 12 hours, or from about 7-10 hours, or from about 8-11 hours, and so on. Preferred is the temperature range from about 90-100 degrees and for a duration in the range of about 5-24 hours.

The solid biomass material was filtered and washed with ethanol. The next step of the extraction/isolation process was alkaline ethanol extraction using 70% ethanol in a liquid:solid ratio 10:1. Alkali was added to such suspension to the final concentration of 1% weight. The suspension was treated at about 70 degree C. for about 3 hours. The solid was then treated with 5% by weight alkali at room temperature for about 10 hours. The filtrate was then treated with enzymes to cleave lignin polysaccharide bonds. Esterases were used for this operation, but any similar enzyme can be used. The isolated glucuronoarabinoxylan was precipitated by ethanol addition and dried.

Carbohydrate analysis using Dionex showed that isolated glucuronoarabinoxylan had 10% molar concentration of arabinose. Preferred are polymers having a concentration of arabinose in the range of about 5-25% molar concentration of arabinose, such as from about 7-20% molar concentration, or from about 12-15% molar concentration of arabinose. NMR analysis showed that samples had 18% molar concentration of 4-O-methyl glucuronic acid. Preferred are polymers with about 5-30% molar concentration of glucuronic acid, including from about 7-25% molar concentration, or from about 10-20% molar concentration, or from about 12-16% molar concentration of glucuronic acid. Especially preferred are polymers having at least 10% molar concentration of arabinose and/or at least 18% molar concentration of 4-O-methyl glucuronic acid.

The molecular weight of the arabinoglucuronoxylan was determined using a HPSEC-MALS-RI-UV aqueous system consisting of a Waters 2690 (Waters Corporation, Milford, Mass., USA). The system had an online degasser; auto sampler; column oven and three serial connected columns (Shodex OHpak SB-803, 804 and 806 M HQ) controlled at 50° C. The detectors were multi-angle laser light scattering (MALS; DSP equipped with a He—Ne laser at 632.8 nm, Wyatt Technology Corp., Santa Barbara, Calif., USA); refractive index (RI) controlled at 35° C. (Optilab DSP, Wyatt Technology Corp.) and a UV-vis detector set to record at 280 nm (Shimadzu SPD-10A, Shi-madzu Corp., Kyoto, Japan). The eluent used was sodium nitrate (0.1 M NaNO3) containing 0.02% sodium azide (NaN3). The flow rate was 0.4 ml/min. All samples were dissolved in 0.1 M NaNO3 solution at a concentration of 2% (w/w) and filtered (GHP syringe filter, 0.45 μm, PALL). The do/dc used was 0.146 ml/g. The range of angles available for determination was 30-150°. The weight-average molecular weight was determined using ASTRA3 software. The SEC was also run in a strongly alkaline sodium hydroxide/acetate solution (0.2 M hydroxide and 0.1 M). The weight average molecular weight $M_w$ was found to be above 12,000 g/mol. Preferred are polymers with a weight average molecular weight $M_w$ in the range of about 8,000-20,000 g/mol, such as from about 10,000-18,000 g/mol, or from about 14,000-16,000 g/mol. Especially preferred biopolymers of the invention comprise a weight average molecular weight $M_w$ of at least 12,000 g/mol. Even further, preferred polymers of the invention can comprise one or more of the characteristics described in this specification.

Example 2

Preparation and Evaluation of Laminate

5% by weight of Spruce Glucuronoarabinoxylan isolated in example 1 was dissolved in water under stirring for 2 hours. The clear solution was casted onto teflon plate and dried 3 days in climate room at 23 degrees C. and 50% RH. Clear and cohesive films were formed without addition of external plasticizer. Films of the invention can be multi-layer films. Especially preferred are layering different types of films having different capabilities to impart one or more desired characteristics into the resultant multi-layered film. The mechanical properties were evaluated in tensile test using 5 samples. The tensile strength was 55 MPa which is remarkably high and elongation to break 2.7%. The films were able to be folded without breaking. The laminates using paper board were prepared by coating of board with 10% by weight solution of Glucuronoarabinoxylan. The laminates were dried in climate room. Excellent adhesion between the film and board carrier was achieved. The oxygen permeability was 0.12 $cm^3$ μm $m^{-2}$ $d^{-1}$ $kPa^{-1}$ as determined using Mocon equipment at 50% RH. In the context of this specification, permeability refers to the transfer of molecules from the product to the external environment, through package or from the external environment through the package, to the product. See "Important Factors for Selecting Food Packaging Materials Based on Permeability," Kay Cooksey, Flexible Packaging Conference, 2004, which is hereby incorporated by reference herein in its entirety. This reference, as well as others cited and incorporated by reference into this specification, form a part of the disclosure herein relating to embodiments of the invention, especially as to any desired characteristic(s) of the food packaging films according to the invention. Other characteristics may be desired, such as a certain water vapor transmission rate, the details of which are provided by the cited references.

The polymers, films, and laminates according to embodiments of the invention are useful for controlled atmosphere storage packaging as well as modified atmosphere packaging, where the interior environment of the packaging is altered especially to slow down growth of unwanted bacteria. In such packaging oxygen can be replaced with nitrogen or carbon dioxide and the environment remain in the controlled state longer due to the low oxygen permeability characteristics of the films prepared according to the invention. Another use for such packaging is to delay the ripening of packaged fruits and vegetables for example by removing oxygen from the package interior and replacing it with carbon dioxide. Such an environment can be maintained due to the low oxygen permeable films of the invention.

Example 3

Acetylated Laminates

The laminate prepared in example 2 was surface acetylated using acetic anhydride. The depth of acetylation was varied by varying time of treatment. An alternative method for achieving acetylated laminates was coating of laminate from example 2 with acetylated Glucuronoarabinoxylans. Such laminates exhibited great flexibility and water resistance. Additional way to prepare water resistant laminates was to prepare films from partially acetylated glucuronoarabinoxylanes in ionic liquids. Such partially acetylated glucuronoarabionoxylanes phase separated upon film formation and formed enrichment of acetylated glucuronoarabinoxylanes at the surface.

The present invention has been described with reference to particular embodiments having various features. It will be apparent to those skilled in the art that various modifications and variations can be made in the practice of the present invention without departing from the scope or spirit of the invention. Indeed, numerous references have been cited in this specification to provide background about the current state of the art. These references can be used by those skilled in the art to supplement this disclosure. To this extent, all of the references cited in this specification are hereby incorporated by reference herein in their entireties to form part of the disclosure of the preferred embodiments of the present invention. For example, any of the desired mechanical properties indicated in the cited references for packaging materials can be the desired properties of the packaging materials of the present invention. One skilled in the art will recognize that the features of embodiments of the invention may be used singularly or in any combination based on the requirements and specifications of a given application or design, and one or more elements, constituents, or process steps may be omitted, incorporated, or altered as desired. Other embodiments of the invention will be apparent to those skilled in the art from consideration of the specification and practice of the invention. It is intended that the specification and examples be considered as exemplary in nature and that variations that do not depart from the essence of the invention are intended to be within the scope of the invention.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. It should be evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A process for obtaining non-cellulosic polysaccharides from biomass comprising:
   refining a biomass by grinding or ball milling;
   performing mild steaming and alkali extraction of the biomass;
   treating the extract by enzymatic treatment; and
   isolating negatively charged non-cellulosic polysaccharides with weight average molecular weight Mw higher than 10,000 g/mol and molecular structure comprising a xylan main chain substituted with more than 15 molar % of 4-O-methyl-glucuronic acid and more than 5 molar % arabinose.

2. A process for isolating glucuronoarabinoxylan from biomass comprising:
   obtaining a biomass;
   optionally mechanically processing the biomass;
   steam treating the biomass at a temperature and under conditions and for a time sufficient to facilitate extraction of non-cellulosic polysaccharides;
   optionally filtering and washing the steam treated biomass with ethanol;
   performing an alkaline ethanol extraction by:
   preparing a mixture by mixing the steam treated biomass with about 70% ethanol in a liquid:solid ratio ranging from about 20:1 to 1:1 and adding alkali to a final concentration of about 1-5% by weight of the mixture;
   optionally heating the mixture at a temperature and under conditions and for a time sufficient to extract non-cellulosic polysaccharides;
   optionally treating the mixture with about 5% by weight alkali at a temperature and under conditions and for a time sufficient to extract non-cellulosic polysaccharides;
   obtaining a filtrate comprising the non-cellulosic polysaccharides and treating the filtrate with one or more enzymes of a type and amount sufficient to cleave lignin polysaccharide bonds to obtain glucuronoarabinoxylan;
   preparing a precipitate of the glucuronoarabinoxylan by ethanol addition, drying the precipitate, and obtaining glucuronoarabinoxylan having at least 10% molar concentration of arabinose, at least 15% molar concentration of 4-O-methyl glucuronic acid, and a weight average molecular weight of at least 10,000 g/mol.

3. The process of claim 2, wherein the biomass is soft wood.

4. The process of claim 2, wherein the biomass steam treating comprises using water at about 95 degrees C. for about 6 hours.

5. The process of claim 2, wherein optionally heating the mixture comprises heating at about 70 degree C. for about 3 hours.

6. The process of claim 2, wherein optionally treating the mixture with about 5% by weight alkali extract comprising treating at room temperature for about 10 hours.

7. The process of claim 2, wherein treating the filtrate with one or more enzymes comprises treating with esterases.

8. A laminate comprising a substrate coated with negatively charged non-cellulosic polysaccharide prepared by the method of claim 1 and exhibiting oxygen barrier properties sufficient for packaging food or oxygen-sensitive materials.

9. A laminate according to claim 8 further coated with acetylated arabinoxylan.

10. A laminate comprising a substrate coated with negatively charged non-cellulosic polysaccharide prepared by the method of claim 1 and further surface acetylated.

11. Food packaging materials comprising at least one laminate produced by the method of claim 1.

12. Industrial product packaging materials comprising at least one laminate produced by the method of claim 1.

13. A laminate comprising a substrate coated with negatively charged non cellulosic polysaccharide prepared by the method of claim 2 and exhibiting oxygen barrier properties sufficient for packaging food or oxygen sensitive materials.

14. A laminate comprising a substrate coated with negatively charged non cellulosic polysaccharide prepared by the method of claim 2 and further surface acetylated.

15. Food packaging materials comprising at least one laminate produced by the method of claim 2.

16. Food packaging materials comprising at least one laminate of claim 8.

17. Industrial product packaging materials comprising at least one laminate produced by the method of claim 2.

18. Industrial product packaging materials comprising at least one laminate of claim 8.

* * * * *